United States Patent [19]

Scheuermann

[11] 3,987,162

[45] Oct. 19, 1976

[54] COMBABILITY OF HAIR WITH WATER-SOLUBLE, HARDENABLE POLYCONDENSATION PRODUCTS

[75] Inventor: Fanny Scheuermann, Dusseldorf, Germany

[73] Assignee: Henkel & Cie G.m.b.H., Dusseldorf, Germany

[22] Filed: Dec. 20, 1974

[21] Appl. No.: 534,806

[30] Foreign Application Priority Data

Dec. 21, 1973 Germany............................ 2363871

[52] U.S. Cl............................ 424/70; 252/DIG. 2; 252/DIG. 3; 252/DIG. 13; 252/114; 252/118; 252/542; 252/544; 252/545; 252/546; 252/547; 424/DIG. 2; 424/71; 424/78; 424/80; 424/81; 424/359; 424/361; 424/362; 424/364; 424/365

[51] Int. Cl.$^2$.......................................... A61K 7/06

[58] Field of Search............... 260/2 BP, 2 EP, 9; 424/DIG. 1, DIG. 2, 47, 70, 71

[56] References Cited

UNITED STATES PATENTS

| | | | |
|---|---|---|---|
| 3,090,727 | 5/1963 | Carter................................ | 424/70 |
| 3,347,803 | 10/1967 | Frotscher et al.................. | 260/2 BP |
| 3,462,383 | 8/1969 | Longoria et al. .................... | 260/9 |
| 3,560,609 | 2/1971 | Korden.............................. | 424/78 X |
| 3,567,420 | 3/1971 | Legator et al. .................... | 424/78 X |
| 3,746,678 | 7/1973 | Dick et al. ......................... | 260/2 BP |
| 3,855,158 | 12/1974 | Petrovich et al.................. | 260/2 BP |

*Primary Examiner*—James O. Thomas, Jr.
*Assistant Examiner*—Vera C. Clarke

[57] ABSTRACT

A hair cosmetic preparation for the shampooing and treatment of hair contains readily soluble, hardenable polycondensation products, the polycondensation products being reaction products of water-soluble polyamines with polyoxyalkylene glycol derivatives, which in turn is reacted with a bifunctional compound which contains more than one epoxide and/or α-halo-β-hydroxy alkyl groups in the molecule, and gives the hair treated therewith excellent, lasting combability, and also softness and body.

2 Claims, No Drawings

COMBABILITY OF HAIR WITH WATER-SOLUBLE, HARDENABLE POLYCONDENSATION PRODUCTS

OBJECTS OF THE INVENTION

It is an object of the present invention to provide a hair cosmetic preparation for the shampooing and treatment of hair, which preparation contains readily soluble synthetic resins having a content of epoxide groups.

It is another object of the present invention to provide a hair cosmetic preparation for the shampooing and treatment of hair, which preparation has a content of readily soluble, hardenable polycondensation products, the polycondensation products being reaction products of water-soluble polyamines with polyoxyalkylene glycols and which in turn is reacted with a bifunctional compound which contains more than one epoxide and/or -halo- -hydroxy alkyl group in the molecule, and which gives the hair treated therewith excellent, lasting combability, and also softness and body.

These and other objects of the present invention will become apparent as the descripttion thereof proceeds.

DESCRIPTION OF THE INVENTION

The present invention relates to hair cosmetic preparations for the shampooing and treatment of hair, which preparations contain readily soluble synthetic resins having a content of polyoxyethylene groups.

It has now been discovered that hair cosmetic preparations for the shampooing and treatment of hair, which preparations have a content of readily soluble, hardenable polycondensation products, the polycondensation products being reaction products of water-soluble polyamines with ethers of polyoxyalkylene glycols having terminal halogens or hydroxyls and with epichlorohydrin or compounds which contain more than one epoxide and/or halohydrin groups in the molecule and which give the hair treated therewith excellent, lasting combability, and also softness and body.

According to the present invention there is superfatting a hair cosmetic preparation for the shampooing and treatment of hair having a content of readily soluble, hardenable polycondensation products, the polycondensation products being reaction products of a water-soluble polyamine with ethers of polyoxyalkylene glycols having terminal halogens or hydroxyls and having more than one reactive hydrogen atom attached to nitrogen which in turn is reacted with a bifunctional compound which contains more than one epoxide and/or -halo- -hydroxyl alkyl groups in the molecule and of other additives comprising protein hydrolyzates, herb extracts, superfating agents, foam stabilizers, acids, salts, perfumes, preservatives, antidandruff agents or film forming hair-strengthening synthetic resins.

More particularly the present invention provides a hair cosmetic preparation composition comprising from 0.1% to 10% by weight based upon the total weight of said composition, of a readily water-soluble, hardenable polycondensation product produced by reacting a polyamine compound having from 2 to 10 carbon atoms with an ether of polyoxyalkylene glycol having terminal halogens or hydroxyls and having from 2 to 4 carbon atoms in the alkylene units thereof, said polyamine reaction compounds having more than one hydrogen atom attached to a nitrogen atom and being further reacted with a bifunctional aliphatic compound having functional groups selected from the group consisting of epoxide and -halo- -hydroxy-alkyl.

Preferably the polycondensation product is a reaction product selected from the group consisting of i. a reaction product of dipropylenetriamine with Polyglycol 1000 bis-chlorohydrin ether, having further been reacted with epichlorohydrin, ii. a reaction product of dipropylenetriamine with Polyglycol 1000 bis-chlorohydrin ether, having further been reacted with a reaction product of epichlorohydrin with Polyglycol 600, iii. a reaction product of diethylenetriamine with ethoxylated ethylene-chlorohydrin, having been further reacted with epichlorohydrin, iv. a reaction product of dipropylenetriamine with ethoxylated glycerin chlorohydrin ether, having been further reacted with epichlorohydrin, v. a reaction product of triethylenetetramine with Polyglycol 1000 bis-chlorohydrin ether, having been further reacted with a reaction product of Polyglycol 600 with epichlorohydrin, vi. a reaction product of dipropylenetriamine having been reacted with Polyglycol 600 bis-chlorohydrin ether, and vii. a reaction product of dipropylenetriamine having been reacted with polyoxyethylene glycol 200 bis-chlorohydrin ether.

In order to produce the hardenable polycondensation products which are to be used in hair cosmetic preparation of the invention for the shampooing and treatment of hair, polyamine compounds such as polyamines having 2 to 10 carbon atoms and polyamines having 2 to 10 carbon atoms containing polyoxyalkylene units are used as starting materials. These are obtained in a known manner from polyamines, especially polyalkylene-polyamines, by reaction with mono-and/or polyfunctional derivatives of polyoxyalkylene glycols. These mono- and/or polyfunctional derivatives of polyoxyalkylene glycols can contain, as reactive groups, chlorohydrin, glycidyl, halogen or other substituents capable of forming anions, such as acid sulfates or lower alkyl sulfonates. The polyoxyalkylene groups present in the polyoxyalkylene glycol derivatives can have various molecular weights, with the starting materials usually being selected so as to have a total of approximately 3 to 70 alkylene oxide units having 2 to 4 carbon atoms in the molecule. Ethylene oxide is preferred as the alkylene oxide, but other alkylene oxides, such as propylene oxide and butylene oxide, and also the corresponding mixtures thereof can be used. The polyalkylene oxide chains may optionally also be interrupted, for example, by the interposition of a dicarboxyl, or diisocyanate.

The polyoxyalkylene glycol derivatives have the formula

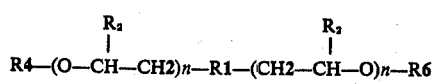

wherein R is a member selected from the group consisting of oxygen, glyceryloxy, lower alkylene dicarboxyloxy and lower alkylene diisocyano; R is a member selected from the group consisting of hydrogen, methyl and ethyl; R is a member selected from the group consisting of -halo- -hydroxyl-lower alkyl, , -epoxylower alkyl, and α-sulfato-lower alkyl; and n is an integer from 2 to 35.

The polyamines have the formula

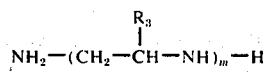

wherein $R_3$ is a member selected from the group consisting of hydrogen and methyl and m is an integer from 1 to 3.

After the polyoxyalkylene glycol derivatives and the polyamines have been reacted in a molar ratio of 1:0.8 to 1:1.5, preferably 1:1.05 to 1:1.2 at a temperature of from 75° to 160° C, the reaction product is further reacted with an aliphatic bifunctional compound containing at least one epoxide or α-halo-β-hydroxy alkyl group.

Suitable compounds for the second reaction component are those containing one or more epoxide and/or halohydrin group in the molecule, such as epichlorohydrin, dichlorohydrins or bifunctional reaction products of these compounds with glycols, diglycols, polyalkyleneoxides, glycerin, dicarboxylic acids of 2 to 6 carbon atoms, polycarboxylic acids of 3 to 6 carbon atoms, or polyhydroxy phenols, having 2 to 4 hydroxy groups.

Preferably these polyfunctional compounds are epichlorohydrin and the above polyoxyalkylene glycol derivatives.

The production of the hardenable polycondensation products, which are to be used in the agents of the invention for the shampooing and treatment of hair can be effected in one operation in a particularly simple manner, in that a polyoxyalkylene glycol is reacted with 2 mols of epichlorohydrin to give a bischlorohydrin ether, which is then caused to react with sufficient polyamine for the number of chlorine atoms in the reaction mixture and the number of amino hydrogen atoms present, to be in the ratio of 4 : 5 to 7 : 5. In this production process, the polyglycolpolyamine which is formed intermediately is not isolated but is reacted directly with further polyoxyalkylene glycol bischlorohydrin ether to give the desired polycondensation product. The reaction of the polyamines containing the polyalkylene oxide residues with the compounds containing more than one epoxide and/or halohydrin group in the molecule, can be effected in the presence of organic solvents, or preferably, in the presence of water.

In order to accelerate the reaction, acid-binding substances, such as alkali metal hydroxides for example sodium hydroxide, alkali metal carbonates for example sodium carbonate, alkaline earth metal carbonates for example magnesium carbonate, lower alkanolamines such as triethanol-amine are also used. The reaction between the polyoxyalkylene glycol and epichlorohydrin is preferably conducted in the presence of an etherification catalyst such as boron trifluoride, tin tetrachloride or sodium hydroxide.

The one stage reaction is carried out at temperatures of between 50° C and 100° C until a substantial increase in the viscosity of the reaction product is brought about. As soon as the desired degree of polycondensation has been attained, at which the reaction product is still readily soluble in water, the reaction is terminated, for example, by adjusting the pH value to below 6.

Isolation of the polycondensation products which are to be used in accordance with the invention in pure form is not necessary, since they can be incorporated into the hair cosmetic preparation for the shampooing and treatment of hain in the form of the viscous, aqueous solution. The concentration of the solutions can be varied with regard to the viscosity of the polycondensation products, but preferably the concentration will not be substantially less than 50%.

The incorporation of the aqueous solution of the polycondensation products into the hair cosmetic preparation for the shampooing and treatment of hair is usually effected simply by stirring in. The amount which is added varies from 0.1% to 10% by weight, preferably being 0.5% to 5% by weight, calculated as pure polycondensation product and based on the total hair cosmetic preparation. An effective amount of the preparation is applied to the hair preferably human hair, at a temperature between 10° C to 40° C, preferably at room temperature.

Of particular importance is the good compatability of the polycondensation products with surface-active agents, particularly anionic surface-active agents, such as higher alkyl sulfates and higher alkyl ether sulfates. This is because it is possible to incorporate an active ingredient, which confers antistatic properties and shine, into shampoos based on anionic surface-active agents. When used in this manner in shampoos according to the invention, the polycondensation product additive impairs neither the viscosity nor the foaming nature or the washing power of the shampoo formulation.

In the simplest case, the compositions according to the invention may contain 0.1% to 10% by weight, preferably 0.5% to 5% by weight of an aqueous or aqueous-alcoholic dispersion of the described substances and in this form may be used, for example, as an after-rinsing preparation. The compositions may be adapted to for other uses, such as for example, hair shampoos, hair dressings, hair setting agents, hair strengtheners, hair medications, hair conditioning agents, hair sprays, medicated rinses and hair tonics, and would therefore contain the customary components used in the usual proportions in these compositions.

Accordingly, the compositions may contain from 0% to about 50% by weight of surface-active components, usually being the anionic sulfate surface-active compounds such as higher fatty alcohol sulfates, higher fatty alcohol ether sulfates optionally having 3 to 4 ethylene oxide units in the molecule, higher alkylphenol ethoxylated sulfates, monoglyceride sulfates, and also higher fatty acid-protein condensation products, higher fatty acid sarcosides and higher fatty acid methyl taurides. Also suitable for special preparations are amphoteric surface-active compounds, such as for example, the imidazole derivatives known by the name Miranols. The above-mentioned anionic surface-active compounds are present preferably in the form of their alkali metal, such as sodium, and triethanolamine salts and in certain cases such as, for example sodium lauryl ether sulfate also in the form of the magnesium salts.

Emulsifying agents which may be present in the compositions from 0% to about 10% by weight according to the invention are soaps of stearic, lauric and oleic acids in the form of their sodium, potassium or alkanolamine salts, as well as the above mentioned anionic sulfate surface-active compounds, and polyol-fatty acid esters, for example glycerine monostearate, propylene glycol monostearate, diethyleneglycol monostearate, some in admixture with anionic emulsifiers, fatty alcohol mixtures in combination with anionic emulsifiers; nonionic emulsifiers such as polyethylene oxide glycol esters, for example polyhydroxyethylene stearate, -laurate or -oleate, polyethylene oxide sorbitan esters, with higher fatty acids, simple sorbitan esters such as sorbitan monolaurate, -oleate, -sesqui-oleate, sterols, polyoxyethylene glycol esters of higher fatty acids, as, for example the mono- and di-laurates, -oleates or stearates of polyoxyethylene glycol with molecular weights of 200 to 600; cationic emulsifiers such as coconut fatty acid diethanolamide, lauryl ammonium chloride, cetyl pryridinium chloride, cetyl trimethylammonium bromide, diisobutyl-phenoxyethoxyethyl-dimethylbenzylammonium chloride, alkyl-dimethylbenzylammonium chloride with 10 to 14 carbon atoms in the alkyl residue, N-(stearylcolaminoformylmethyl)-pyridinium chloride or the like; examples of amphoteric emulsifiers are ethylene-cycloimido-1-lauryl-2-hydroxyethylene-sodium alcoholate, triethanolamine-β-alamine, N-lauryl-aminopropionate, N-lauryliminodipropionate, N-lauryl-diethyl-triaminoacetic acid, etc.

The usual substances may also be added as thickeners, which are present from 0% to about 5% by weight, such as, for example, higher fatty alcohols such as cetyl alcohol, cetyl stearyl alcohol or oleyl-cetyl alcohol mixtures; esters of higher fatty acids with higher fatty alcohols such as decyl oleate; sodium alginates, fatty acid alkylolamides and some partial tylose slimes; also higher molecular weight polyoxyethylene-glycol-mono- or -di-esters of higher fatty acids, such as stearic acid and lauric acid. In some cases, electrolytes such as sodium chloride or ammonium chloride are also used as thickeners in combination with alkyl polyoxyethylene sulfates.

In specified cases, superfatting agents may also be added to the compositions according to the invention, in amounts of from 0% to about 5% by weight for example polyhydroxyethylated lanolin derivatives, lecithin derivatives or the already mentioned alkylolamides, to which a certain oiling action belongs. The latter may also serve as foam stabilizers in shampoos.

The compositions according to the invention may also contain loer aliphatic alcohols as solvents, such as lower alkanols of 1 to 6 carbon atoms for example ethanol or isopropanol. So-called builder components may be added from 0% to about 15% by weight, such as paraffin, fats, lanolin and wool fat alcohols. Other usual components may be added from 0% to about 7% by weight, such as perfumes; preservatives, especially formalin, sorbic acid and dehydroacetic acid, 6-acetoxy-2,4-dimethyl-dioxane, esters of p-hydroxy-benzoic acid; and biogenic substances such as plant extracts and vitamin complexes. Solution aid components may be added from 0% to about 10% by weight, such as lower alkylene glycols, for example 1,3-propanediol, 1,3-butyleneglycol, diethyleneglycol. Hair strengthening synthetic resins which are film forming components may be added from 0% to about 5% by weight such as polyvinylpyrrolidone, vinylpyrrolidone-vinyl acetate copolymers, polymers of the acrylic acid series, dimethylhydantoinformaldehyde resins and polymers of the 2-alkyl-2-oxazoline series. Acid adjusting agents, especially fruit acids, such as citric acid and/or lactic acid may be added from 0% to about 2% by weight.

Antidandruff agents may be added from 0% to 5% by weight, and protein hydrolyzates may be added from 0% to 2% by weight.

The hair cosmetic preparations according to the invention for the shampooing and treatment of hair give the hair which is treated therewith, such as living hair, preferably human hair, extraordinarily advantageous properties with regard to the usual measures for the care of hair. Thus the combability of the hair while wet is substantially improved. The dry hair is soft and pleasant in texture, having good body, and capable of being dressed without difficulty. The static charge of the dry hair is reduced to a minimum. A particularly advantageous feature is that the treated hair retains these properties, which are favorable with respect to the dressing of the hair, over quite a long period of time, generally from one washing to another, in almost undiminished quality.

The following examples are merely illustrative of the present invention without, however, being deemed limitative in any manner thereof.

EXAMPLE 1

The production of several polycondensates is to be first of all described; and subsequently the manner in which they can be used in the agents according to the invention for the shampooing and treatment of hair will be described.

PRODUCT A 300 gm of Polyglycol 1000, a polyoxyethylene glycol having an average molecular weight of about 1000, (0.3 mol), was melted in a flask provided with a stirring means, a reflux condenser and a thermometer; and while being stirred, the melt was mixed together with 6 gm of boron trifluoride in the form of an approximately 20% solution in ether. While the reflux condenser cooling was shut off, the mixture was heated to approximately 70° C, in the course of which most of the ether was distilled off. Then, with reflux condenser cooling 55 gm of epichlorohydrin (0.6 mol) was then added. During continuous stirring the temperature was maintained at 68° C to 75° C for 30 minutes with refluxing. 44 gm of dipropylenetriamine was then added to the raw polyoxyethylene glycol-bis-chlorohydrin ether which had been prepared and the temperature was raised to 120° C to 130° C. This temperature was maintained for approximately one hour. The reaction mixture was then cooled to 90° C to 95° C, and 135 gm of water was stirred in, and the stirring was continued for approximately 30 minutes at 90° C to 95° C until the pH value of the reaction mixture had dropped to below 8.5. After cooling to a temperature of approximately 60° C had been effected, 30 gm of epichlorohydrin was added and the reaction mixture was maintained at this temperature for a sufficient length of time (50 to 60 minutes) for the pH value to drop to approximately 7. The pH value was then adjusted to 6 with formic acid. Water was then added to the reaction product to give 600 gm of finished product.

A viscous yellowish liquid was obtained which could be mixed with water.

PRODUCT B 100 gm of Polyglycol 1000 (0.1 mol) was placed in a flask provided with a reflux condenser, thermometer and a stirring means; and 2 gm of boron trifluoride was mixed in utilizing a procedure analogous to that described for Product A. 18.5 gm of epichlorohydrin was then added at 70° C and stirring was continued for one hour at 68° C to 75° C. 14.5 gm of dipropylenetriamine, 60 gm of water and 12.5 gm of 40% caustic soda solution was added to the reaction mixture which had been obtained and which basically consisted of bischlorohydrin ether of Polyglycol 1000 and also a minor amount of the monochlorohydrin ether of Polyglycol 1000. The mixture was then heated for 50 minutes at 90° C to 100° C. The subsequent pH value was approximately 9.4. At this point of time the titration of a sample revealed that approximately 90% of the organically combined chlorine which was used had been converted into ionic chlorine. 82 gm of a raw bischlorohydrin ether of Polyglycol 600, which was obtained in the abovedescribed manner by the reaction of 2 mols of epichlorohydrin on 1 mol of Polyglycol 600, a polyoxyethylene glycol having an average molecular weight of about 600, was added. Subsequent stirring was effected for approximately 1.5 hours while refluxing at the boiling point (about 100° C). At the end of this period the pH value of the mixture had dropped to approximately 7.2. The reaction mixture had become extremely viscous. Then, with the addition of approximately 7.5 gm of 36% hydrochloric acid, the mixture was adjusted to pH 5.5 to 6 and was made up to 320 gm with water.

A viscous but readily flowing, yellowish liquid was obtained which mixes with water in any ratio.

PRODUCT C 290 gm (about 0.3 mol) of a reaction product of 1 mol of ethylene-chlorohydrin and 20 mols of ethylene oxide were heated and stirred for 4 hours at a temperature of 120° C with 31 gm (about 0.3 mol) of diethylenetriamine in a flask provided with a reflux condenser. The reaction mixture was then cooled to approximately 60° C. 100 gm of water and 55 gm of epichlorohydrin was added and stirring was then continued at 55° C to 65° C for a sufficient length of time (1.5 to 2 hours) for the pH value of the reaction mixture to drop to approximately 7. The viscous product which was obtained was adjusted to pH 6 with hydrochloric acid and made up to 510 gm with water.

PRODUCT D 5.25 parts by weight of boron trifluoride were slowly added during stirring and at room temperature to 260 parts by weight of a glycerin-ethoxylation product, which at normal temperature is liquid, and was obtained by ethoxylation of 1 mol of glycerin with 30 mols of ethylene oxide. 28 parts by weight of epichlorohydrin was then added. While being stirred, the mixture was heated to 68° C to 70° C and was maintained at this temperature for one hour. 20 parts by weight of dipropylenetriamine and 120 parts by weight of water were then added. The mixture which was obtained was stirred while refluxing at the boiling point (about 100° C) for approximately 20 minutes. 60 parts by weight of 10% caustic soda solution was added, and the mixture was maintained at the boiling point for a further hour. Cooling to a temperature of approximately 65° C was then effected. After 14 parts by weight of epichlorohydrin had been added, subsequent stirring was effected for approximately one hour at 60° C to 70° C until the pH value of the mixture had dropped to about 7 to 7.5. After the pH value had been adjusted to 5.5 to 6 with about 14 gm of 30% hydrochloric acid, the mixture was made up to 750 gm with water.

A honey-colored, viscous, clear liquid, which mixes with water in any ratio was obtained.

PRODUCT E 100 parts by weight of Polyglycol 1000 (0.1 mol) were melted in a vessel provided with a stirring means, a thermometer and a reflux condenser, and were mixed with 2 parts by weight of boron trifluoride using a procedure analogous to that described for Product A. 14 parts by weight of epichlorohydrin (0.15 mol) were then added. After stirring had been effected for one hour at 68° C to 72° C, 14 parts by weight of triethylenetetramine and 70 parts by weight of water were added; and the mixture was heated under reflux for approximately 20 minutes. 25 parts by weight of 40% caustic soda solution was then added; and the mixture was maintained at the boiling point for a further 30 minutes.

82 parts by weight of a raw bis-chlorohydrin ether of Polyglycol 600, which was prepared by the reaction of 1 mol of Polyglycol 600 with 2 mols of epichlorohydrin in the presence of boron trifluoride were then added. After the mixture has been stirred for one hour at the boiling point, 4.6 parts by weight of epichlorohydrin were added. Stirring was then continued until the pH value had dropped to about 7 to 7.5. The pH value was then adjusted to 5.5 to 6 with concentrated hydrochloric acid, and the mixture was made up to 320 parts by weight with water.

A pale yellow, cloudy, viscous liquid was obtained.

PRODUCT F 180 kg of liquid Polyglycol 600 is placed in a heatable and coolable stirring vessel provided with a reflux condenser and a thermometer. At a temperature of approximately 30° C, 2.7 kg of tin tetrachloride was slowly poured in during stirring. After heating had been effected to 68° C to 70° C, 56 kg of epichlorohydrin was added at a rate such that, while constantly being stirred and possibly cooled, the temperature of the mixture remained between 68° C to 70° C. Stirring was effected for another hour at temperatures in the region of 70° C. The total amount of raw Polyglycol 600 -bis-chlorohydrin ether obtained was approximately 239 kg.

80 kg of the raw Polyglycol 600 -bis-chlorohydrin ether obtained was drawn off into a second heatable and coolable vessel provided with a stirring means, a thermometer and a reflux condenser and having a volume of 600 liters, and during stirring was mixed with 13.2 kg of dipropylenetriamine, 50 kg of water and 28 kg of caustic soda solution (40%). It was then heated for 45 minutes at the boiling point while refluxing. The remaining amount of raw bis-chlorohydrine ether of Polyglycol 600 in the first container was then added during stirring, and after a further 30 kg of water had been added the mixture was again maintained at the boiling point for 20 to 30 minutes. During this time, the pH value of the viscous reaction product dropped to approximately 7.2. Intense cooling was then effected. During cooling the pH value was adjusted to 5.5 to 6 by the addition of approximately 38 kg of 10% aqueous hydrochloric acid.

Approximately 500 kg of a pale yellow, slightly cloudy, highly viscous liquid was obtained.

PRODUCT G 180 kg of Polyglycol 600 was reacted, utilizing a procedure analgous to that described for Product F, with 56 kg of epichlorohydrin in the presence of tin tetrachloride. After 13.2 kg of dipropylenetriamine, 35 kg of 40% caustic soda solution and 150 kg of water had been added, the mixture was heated for approximately 40 minutes at the boiling point while refluxing. After this length of time the pH value of the viscous reaction mixture had dropped to 7.2. The pH value was then adjusted to approximately 5.5 with about 66 kg of 10% hydrochloric acid.

Approximately 500 kg of a cloudy, virtually colorless product was obtained.

PRODUCT H 60 gm of a polyoxyethylene glycol having a molecular weight of 200 was placed in a flask provided with a stirring means, a reflux condenser and a thermometer. 1.7 gm of boron trifluoride-acetic acid (36% $BF_3$) was stirred in; the mixture was heated to 70° C and then 56 gm of epichlorohydrin was added dropwise so that, with appropriate cooling, the reaction temperature could be maintained between 68° C and 72° C. Subsequently, in order to complete the reaction, the mixture was restirred for 30 minutes at 70° C. 13.2 gm of dipropylenetriamine, 80 gm of water and 35 gm of caustic soda solution (37%) was then stirred in. The mixture was heated to 88° C to 90° C and was then stirred at this temperature until the pH value had dropped to 6.9 and approximately 55% of the organically combined chlorine had been converted into the ionic form. The pH value was then adjusted to 5.2 with formic acid, and the final weight was made up to 275 gm with water.

A pale yellow, viscous product was obtained, which dissolved clearly in water.

EXAMPLE 2

Several recipes for hair cosmetic preparations according to the invention having a content of the above-mentioned polycondensation products are listed hereinafter. It is to be understood that these examples of use are merely illustrative of the present invention without being deemed limitative in any manner. All parts are by weight unless indicated otherwise.

HAIR STRENGTHENER

| | Parts |
|---|---|
| Product F | 1.0 |
| Copolymer of vinylpyrrolidone/ vinyl acetate 30:70 | 1.5 |
| Ethanol | 50.0 |
| Perfume | 1.0 |
| Water | 46.5 |

Instead of Product F, all the other above-mentioned products can be used in the appropriate quantity with equally good results.

MEDICATED RINSE FOR HAIR

| | Parts |
|---|---|
| Cetyl alcohol | 3.0 |
| Vaseline | 2.0 |
| Product B | 5.0 |
| Fatty amine derivative having betaine structure, commercial product Dehyton AB 30 of Henkel & Cie. | 5.0 |
| Citric acid | 1.0 |
| Plant extracts | 1.0 |
| Perfume | 1.0 |

MEDICATED RINSE FOR HAIR -continued

| | Parts |
|---|---|
| Water | 82.0 |

The other products can also be used instead of Product B with equally good results.

RAPID HAIR MEDICAMENT

| | Parts |
|---|---|
| Cetyl alcohol | 6.0 |
| Product A | 8.0 |
| Decyl oleate | 3.0 |
| Fatty amine derivative having betaine structure - commercial product Dehyton AB 30 | 5.0 |
| Citric acid | 1.0 |
| Plant extracts | 1.0 |
| Perfume | 1.0 |
| Water | 75.0 |

All of the other above-mentioned products can be used instead of Product A with equally good results.

SHAMPOO

| | Parts |
|---|---|
| Sodium lauryl ether sulfate having 27/28% of active washing substance | 30.0 |
| Sodium chloride | 2.0 |
| Coconut fatty acid diethanolamide | 2.0 |
| Product G | 5.0 |
| Antidandruff active ingredient | 1.0 |
| Protein hydrolyzate | 1.0 |
| Perfume | 1.0 |
| Water | 58.0 |

All of the other above-mentioned products can be used instead of Product G with equally good results.

SHAMPOO

| | Parts |
|---|---|
| Sodium lauryl ether sulfate having 35 to 37% of active washing substance | 30.0 |
| Sodium chloride | 1.0 |
| Product H | 5.0 |
| Perfume | 1.0 |
| Water | 63.0 |

All of the other above-mentioned products can be used instead of Product H with equally good results.

SHAMPOO FOR OILY HAIR

| | Parts |
|---|---|
| Magnesium lauryl ether sulfate having 29 to 31% active washing substance | 30.0 |
| Coconut fatty acid diethanolamide | 5.0 |
| Product D | 5.0 |
| Tactocut-powder M 71 produced by Stockhausen | 3.0 |
| Protein hydrolydate | 1.0 |
| Preservative | 0.2 |
| Perfume | 1.0 |
| Water | 54.8 |

The other above-mentioned products can be used instead of Product D with equally good results.

HAIR CONDITIONER

|  | Parts |
|---|---|
| Cetyl stearyl alcohol | 4.0 |
| Product C | 3.0 |
| Citric acid | 1.0 |
| Preservative | 0.2 |
| Perfume | 1.0 |
| Water | 90.8 |

Product C can be replaced by each of the other above-mentioned products with equally good results.

HAIR SPRAY

|  | Parts |
|---|---|
| Copolymer of vinylpyrrolidone/ vinyl acetate 60:40 | 4.0 |
| Product E | 2.0 |
| Perfume | 2.0 |
| Ethanol (96%) | 92.0 |

Filling: 40% hair lacquer, 60% propellant gas 11/12 (50 : 50). It is possible for Product E to be replaced by any of the other above-mentioned products with equally good results.

DANDRUFF TREATMENT TONIC

|  | Parts |
|---|---|
| Oleyl cetyl alcohol | 0.5 |
| Isopropanol | 62.0 |
| Plant extracts | 4.0 |
| Menthol | 0.2 |
| Protein hydrolyzate | 1.0 |
| Pantothenic acidic calcium | 0.05 |
| Vitamin H | 0.30 |
| Product A | 4.0 |
| Perfume | 1.0 |
| Water | 27.0 |

The other above-mentioned products can be used instead of product A with equally good results.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

I claim:

1. A process for treating hair to improve the combability thereof which comprises applying thereto at a temperature between 10° C to 40° C an effective amount of aqueous dispersion comprising 0.1% to 10% by weight of a readily water-soluble, hardenable polycondensation product selected from the group consisting of
   i. the reaction product of dipropylenetriamine, bis-chlorohydrin ether of polyoxyethylene glycol having an average molecular weight of about 1,000 and epichlorohydrin,
   ii. the reaction product of dipropylenetriamine, bis-chlorohydrin ether of polyoxyethylene glycol having an average molecular weight of about 1,000, and bis-chlorohydrin ether of polyoxyethylene glycol having an average molecular weight of about 600,
   iii. the reaction product of diethylenetriamine, ethoxylated ethylene chlorohydrin, and epichlorohydrin,
   iv. the reaction product of dipropylenetriamine, ethoxylated glycerin chlorohydrin ether, and epichlorohydrin,
   v. the reaction product of triethylenetetramine, bis-chlorohydrin ether of polyoxyethylene glycol having an average molecular weight of about 1,000, and bis-chlorohydrin ether of polyoxyethylene glycol having an average molecular weight of about 600,
   vi. the reaction product of dipropylenetriamine and bis-chlorohydrin ether of polyoxyethylene glycol having an average molecular weight of about 600, and
   vii. the reaction product of dipropylenetriamine and bis-chlorohydrin ether of polyoxyethylene glycol having an average molecular weight of about 200 wherein the ratio of chlorine atoms to amino hydrogen atoms in the reaction products is 4:5 to 7:5.

2. The process according to claim 1 wherein the aqueous dispersion further contains from 0% to about 50% by weight of a surface-active agent; from 0% to about 5% by weight of a thickener; from 0% to about 15% by weight of a builder selected from the group consisting of paraffin, fats, lanolin and wool fat alcohols; from 0% to about 10% by weight of a solution aid component; from 0% to about 2% by weight of an acid; from 0% to about 5% by weight of a hair strengthening film forming synthetic resin; from 0% to about 7% by weight of a component selected from the group consisting of a perfume and a preservative; and from 0% to 2% by weight of a protein hydrolyzate.

* * * * *